(12) United States Patent
Assmann et al.

(10) Patent No.: US 8,778,837 B2
(45) Date of Patent: Jul. 15, 2014

(54) USE OF ACTIVE SUBSTANCE COMBINATIONS FOR CONTROLLING ANIMAL PESTS

(75) Inventors: Lutz Assmann, Langenfeld (DE); Ulrike Wachendorff-Neumann, Neuwied (DE); Heike Hungenberg, Langenfeld (DE); Wolfgang Thielert, Odenthal (DE)

(73) Assignee: Bayer CropScience AG, Monheim (DE)

( * ) Notice: Subject to any disclaimer, the term of this patent is extended or adjusted under 35 U.S.C. 154(b) by 203 days.

(21) Appl. No.: 12/743,473

(22) PCT Filed: Nov. 27, 2008

(86) PCT No.: PCT/EP2008/010069
§ 371 (c)(1),
(2), (4) Date: May 18, 2010

(87) PCT Pub. No.: WO2009/074230
PCT Pub. Date: Jun. 18, 2009

(65) Prior Publication Data
US 2010/0248961 A1 Sep. 30, 2010

(30) Foreign Application Priority Data
Dec. 11, 2007 (EP) .................................. 07122955

(51) Int. Cl.
| | | |
|---|---|---|
| *A01N 25/26* | (2006.01) | |
| *A01N 59/00* | (2006.01) | |
| *A01N 43/00* | (2006.01) | |
| *A01N 43/64* | (2006.01) | |
| *A01N 43/66* | (2006.01) | |
| *A01N 43/78* | (2006.01) | |
| *A01N 43/56* | (2006.01) | |
| *A61K 31/535* | (2006.01) | |
| *A61K 31/44* | (2006.01) | |
| *A61K 31/425* | (2006.01) | |
| *A01N 43/80* | (2006.01) | |

(52) U.S. Cl.
CPC ........................................ *A01N 43/80* (2013.01)
USPC ........... 504/123; 504/124; 504/125; 514/183; 514/229.2; 514/242; 514/245; 514/277; 514/341; 514/342; 514/365; 514/372; 514/407

(58) Field of Classification Search
None
See application file for complete search history.

(56) References Cited

U.S. PATENT DOCUMENTS

| | | | | |
|---|---|---|---|---|
| 4,792,563 A | * | 12/1988 | Whittle ......................... | 514/345 |
| 4,943,434 A | * | 7/1990 | Lidert ........................... | 424/761 |
| 5,604,121 A | * | 2/1997 | Hilder et al. .................. | 424/94.4 |
| 7,309,711 B2 | * | 12/2007 | Dahmen et al. ............... | 514/341 |
| 7,781,648 B2 | * | 8/2010 | Wang et al. .................... | 800/312 |
| 7,868,025 B2 | * | 1/2011 | Dutzmann et al. ............ | 514/341 |
| 2006/0205680 A1 | * | 9/2006 | Dahmen et al. ................ | 514/28 |

FOREIGN PATENT DOCUMENTS

| | | | |
|---|---|---|---|
| WO | WO 2005/009131 A1 | | 2/2005 |
| WO | WO-2005009131 | * | 2/2005 |
| WO | WO 2007/101541 A2 | | 9/2007 |

OTHER PUBLICATIONS

International Search Report of International Application No. PCT/EP2008/010069. European Patent Office, Rijswijk, Netherlands, mailed Apr. 22, 2009.
International Preliminary Report on Patentability and Written Opinion of the International Searching Authority for International Application No. PCT/EP2008/010069, The International Bureau of WIPO, Geneva, Switzerland, issued on Jul. 6, 2010.
Office Action mailed Aug. 15, 2012, in U.S. Appl. No. 12/699,246, Assmann, L., et al., filed Feb. 3, 2010.
Office Action mailed Jan. 14, 2013, in U.S. Appl. No. 12/699,246, Assmann, L., et al., filed Feb. 3, 2010.
Office Action mailed Jan. 6, 2012, in U.S. Appl. No. 12/448,147, Hungenberg, H. et al., filed Aug. 4, 2009.
Office Action mailed Apr. 27, 2012, in U.S. Appl. No. 12/448,147, Hungenberg, H. et al., filed Aug. 4, 2009.
Office Action mailed May 9, 2012, in U.S. Appl. No. 12/743,409, Assmann, L., et al., filed Aug. 17, 2010.
Office Action mailed Sep. 24, 2012, in U.S. Appl. No. 12/974,820, Andersch, W., et al., filed Dec. 21, 2010.
Office Action mailed Oct. 2, 2012, in U.S. Appl. No. 12/452,090, Hungenberg, H., et al., filed Dec. 14, 2009.
Office Action mailed Nov. 19, 2012, in U.S. Appl. No. 12/743,409, Assmann, L., et al., filed Aug. 17, 2010.

* cited by examiner

*Primary Examiner* — Alton Pryor
(74) *Attorney, Agent, or Firm* — Sterne, Kessler, Goldstein & Fox P.L.L.C.

(57) ABSTRACT

The invention relates to the novel use of known active substance combinations which consist firstly of 3,4-dichloro-2'-cyano-1,2-thiazole-5-carboxanilide, of the formula

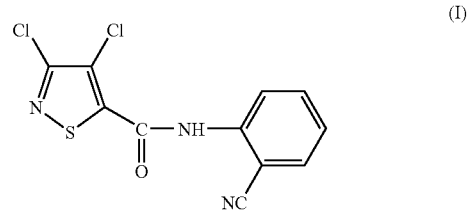

which is known, and secondly further known insecticidal active substances, for controlling animal pests, especially arthropods, in particular insects.

39 Claims, No Drawings

USE OF ACTIVE SUBSTANCE COMBINATIONS FOR CONTROLLING ANIMAL PESTS

The invention relates to the novel use of known active substance combinations which consist firstly of 3,4-dichloro-2'-cyano-1,2-thiazole-5-carboxanilide, which is known, and secondly further known insecticidal active substances, for controlling animal pests, especially arthropods, in particular insects.

It has already been disclosed that 3,4-dichloro-2'-cyano-1,2-thiazole-5-carboxanilide (common name isotianil) has fungicidal properties and is suitable for controlling animal pests (cf. WO 99-024 413). While the activity of this substance is good, it sometimes leaves something to be desired when used at low application rates.

It has furthermore also been disclosed that a large number of neonicotinyls, carbamates, pyrethroids and phenylpyrazoles can be employed for controlling insects (cf. EP-A 0 192 060, EP-A 0 580 553, Pesticide Manual, 11th Edition (1997) No. 109, 110, 172, 323 and 376 and also DE-A 196 53 417). The insecticidal activity of these substances is good.

It has now been found that active substance combinations which are known from WO 2005/009131 of (A) compound 3,4-dichloro-2'-cyano-1,2-thiazole-5-carboxanilide (isotianil), of the formula

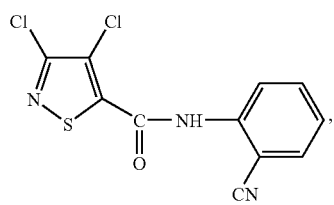

(I)

and
(1) a neonicotinyl of the formula

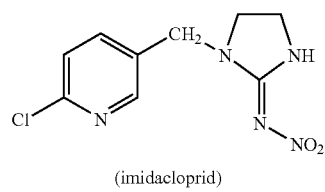

(imidacloprid) (II-a)

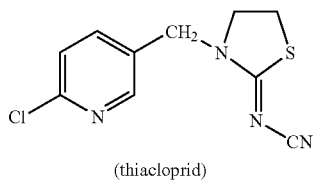

(thiacloprid) (II-b)

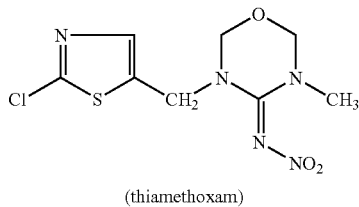

(thiamethoxam) (II-c)

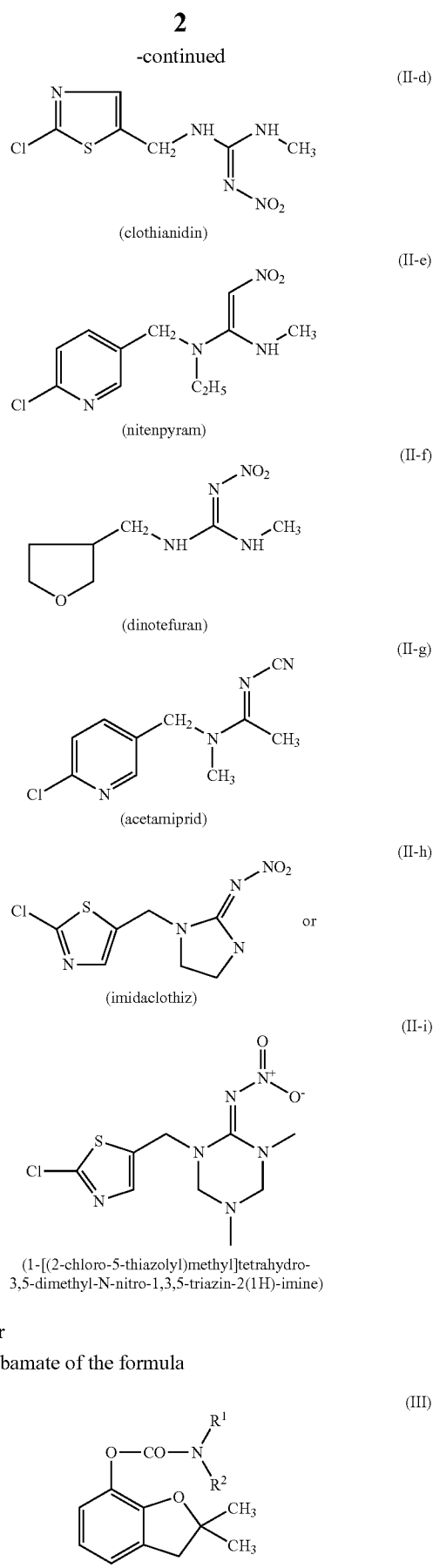

(clothianidin) (II-d)

(nitenpyram) (II-e)

(dinotefuran) (II-f)

(acetamiprid) (II-g)

(imidaclothiz) (II-h) or (1-[(2-chloro-5-thiazolyl)methyl]tetrahydro-3,5-dimethyl-N-nitro-1,3,5-triazin-2(1H)-imine) (II-i)

and/or
(2) a carbamate of the formula (III)

in which the radicals $R^1$ and $R^2$ have the following meanings:

$R^1 = $ —S—N(CH(CH$_3$)$_2$)—CH$_2$—CH$_2$—CO—OCH$_2$—CH$_3$ (III-a)

$R^2 = CH_3$ (benfuracarb)

$R^1 = $ —S—N(CH$_3$)—CO—O—(CH$_2$)$_3$—CH$_3$ (III-b)

$R^2 = CH_3$ (furathiocarb)

$R^1 = CH_3$ (III-c)

$R^2 = H$ (carbofuran)

or $R^1 = $ —S—N[—(CH$_2$)$_3$—CH$_3$]$_2$ (III-d)

$R^2 = CH_3$ (carbosulfan)

and/or (3) a phenylpyrazole derivative of the formula (IV)

in which the radical $R^3$ has the following meaning:

$R^3 = $ —CF$_3$ (IV-a)

(fipronil)

or $R^3 = C_2H_5$ (IV-b)

(ethiprole)

and/or (4) a pyrethroid of the formula (V)

(cycloprothrin)

and/or (5) a pyrethroid derivative of the formula (VI-a)

(etofenprox)

or (VI-b)

(silafluofen)

and/or (6) the dithiol derivative of the formula (VII)

(cartap)

and/or (7) the triazine derivative of the formula (VIII)

(pymetrozine)

and/or (8) a macrolide derivative
  with the common name spinosad (IX-a) or
  with the common name spinetoram (IX-b)
  are well suited for use in the control of animal pests, especially arthropods, in particular insects.
  Surprisingly, the insecticidal activity of the active substance combinations according to the invention is considerably higher than the total of the activities of the individual active substances. This means that a true synergistic effect, which could not have been predicted, exists, not simply a compilation of activity.
  3,4-Dichloro-2'-cyano-1,2-thiazole-5-carboxanilide (isotianil), of the formula (I), has been disclosed (cf. WO 99-24 413).

The components which are also present in the active substance combinations according to the invention, besides the active substance of the formula (I), are also known. Specifically, the active substances are described in the following publications:

(1) Compounds of the formulae (II-a) to (II-i)
  EP-A 0 192 060
  EP-A 0 235 725
  EP-A 0 580 553
  EP-A 0 376 279
  Pesticide Manual, 11th Edition (1997), No. 521
  EP-A 0 649 845
  Pesticide Manual, 11th Edition (1997), No. 5
  EP-A 0 192 060
  EP-A 0 428 941
(2) Compounds of the formulae (IIIa) to (III-d)
  Pesticide Manual, 11th Edition (1997), No. 58, No. 376, No. 109 and No. 110
(3) Compounds of the formulae (IVa) and (IV-b)
  Pesticide Manual, 11th Edition (1997), No. 323
  DE-A 196 53 417
(4) Compound of the formula (V)
  Pesticide Manual, 11th Edition (1997), No. 172
(5) Compounds of the formulae (VI-a) and (VI-b)
  DE-A 3 117 510
  Pesticide Manual, 11th Edition (1997), No. 650
(6) Compound of the formula (VII)
  Pesticide Manual, 11th Edition (1997), No. 113
(7) Compound of the formula (VIII)
  EP-A 0 314 615
(8) Compounds of the formula (IX-a) and (IX-b)
  EP-A 0 375 316
  WO-A 1997/00265

Besides the active substance of the formula (I), the active substance combinations according to the invention contain at least one active substance of the compounds from groups (1) to (8).

When the active substances are present in certain weight ratios in the active substance combinations according to the invention, the synergistic effect becomes particularly pronounced. However, the weight ratios of the active substances in the active substance combinations can be varied within a relatively wide range. In general,
  0.001 to 1000 parts by weight, preferably 0.01 to 100 parts by weight, of active substance from group (1),
  1 to 500 parts by weight, preferably 10 to 100 parts by weight, of active substance from group (2), 0.001 to 1000 parts by weight, preferably 0.01 to 100 parts by weight, of active substance from group (3),
  0.5 to 50 parts by weight, preferably 1 to 20 parts by weight, of active substance from group (4),
  0.5 to 50 parts by weight, preferably 5 to 20 parts by weight, of active substance from group (5),
  1 to 500 parts by weight, preferably 2 to 20 parts by weight, of active substance from group (6),
  1 to 100 parts by weight, preferably 1 to 30 parts by weight, of active substance from group (7),
  0.5 to 50 parts by weight, preferably 1 to 20 parts by weight, of active substance from group (8)
are used per part by weight of active substance of the formula (I).

In addition,
  0.0016 to 625 parts by weight, preferably 0.008 to 125 parts by weight, and especially preferably 0.04 to 25 parts by weight, and very especially preferably 0.2 to 5 parts by weight, of active substance from group (1),
  0.0016 to 625 parts by weight, preferably 0.008 to 125 parts by weight, and especially preferably 0.04 to 25 parts by weight, and very especially preferably 0.2 to 5 parts by weight of active substance from group (2),
  0.0016 to 625 parts by weight, preferably 0.008 to 125 parts by weight, and especially preferably 0.04 to 25 parts by weight, and very especially preferably 0.2 to 5 parts by weight of active substance from group (3),
  0.0016 to 625 parts by weight, preferably 0.008 to 125 parts by weight, and especially preferably 0.04 to 25 parts by weight, and very especially preferably 0.2 to 5 parts by weight of active substance from group (4),
  0.0016 to 625 parts by weight, preferably 0.008 to 125 parts by weight, and especially preferably 0.04 to 25 parts by weight, and very especially preferably 0.2 to 5 parts by weight of active substance from group (5),
  0.0016 to 625 parts by weight, preferably 0.008 to 125 parts by weight, and especially preferably 0.04 to 25 parts by weight, and very especially preferably 0.2 to 5 parts by weight of active substance from group (6),
  0.0016 to 625 parts by weight, preferably 0.008 to 125 parts by weight, and especially preferably 0.04 to 25 parts by weight, and very especially preferably 0.2 to 5 parts by weight of active substance from group (7),
  0.0016 to 625 parts by weight, preferably 0.008 to 125 parts by weight, and especially preferably 0.04 to 25 parts by weight, and very especially preferably 0.2 to 5 parts by weight of active substance from group (8)
are used per part by weight of active substance of the formula (I).

Furthermore, the active substance of the formula (I) may also be present in the following weight ratios together with the active substances from groups (1) to (8): 900:1 to 1:900, 800:1 to 1:800, 700:1 to 1:700, 600:1 to 1:600, 500:1 to 1:500, 400:1 to 1:400, 300:1 to 1:300, 250:1 to 1:250, 200:1 to 1:200, 100:1 to 1:100, 90:1 to 1:90, 80:1 to 1:80, 70:1 to 1:70, 60:1 to 1:60, 40:1 to 1:40, 30:1 to 1:30, 10:1 to 1:10, 5:1 to 1:5, 4:1 to 1:4, 3:1 to 1:3.

Within the scope of the present invention, the term "active substance combination" represents various combinations of compound (A) of the formula (I) and active substances from the abovementioned groups (2) to (8), for example in the form of a single ready-mix, in a combined spray mixture consisting of separate formulations of the individual active substances, for example a tank mix, or in a combined use of the individual active substances when these are applied sequentially, for example one after the other within a suitably short period, for example a few hours or days. In accordance with a preferred embodiment, the sequence of the application of the compound (A) of the formula (I) and active substances from the abovementioned groups (2) to (8) is not critical for carrying out the present invention.

In the use according to the invention of the active substance combinations as insecticides and acaricides, the application rates can be varied within a substantial range, depending on the type of application. In the treatment of plant parts, for example leaves, the application rate of the active substance combinations is from 0.1 to 10 000 g/ha, preferably from 10 to 1000 g/ha, especially preferably from 25 to 300 g/ha (in the case of application by pouring or drip application, the application rate can even be reduced, especially when inert substrates such as rock wool or perlite are used); in the treatment of seed, it is from 2 to 200 g per 100 kg of seed, preferably from 3 to 150 g per 100 kg of seed, especially preferably from 2.5 to 25 g per 100 kg of seed, very especially preferably from 2.5 to 12.5 g per 100 kg of seed; in the case of soil treatment, it is from 0.1 to 10 000 g/ha, preferably from 1 to 5000 g/ha.

These application rates are only mentioned by way of example and not by way of limitation within the meaning of the invention.

The active substance combinations according to the invention can be employed for protecting plants within a certain period of time after the treatment from attack by the above-mentioned animal pests. The period of time within which protection is effected generally extends to 1 to 28 days, preferably to 1 to 14 days, especially preferably to 1 to 10 days, very especially preferably to 1 to 7 days after the treatment of the plants with the active substances, or to up to 200 days after seed treatment.

The active substance combinations according to the invention are well tolerated by plants, have favourable toxicity to warm-blooded species, show good environmental compatibility and are suitable for protecting plants and plant organs, for increasing yields, for improving the quality of the harvest crop and for controlling animal pests, in particular insects, arachnids, helminths, nematodes and molluscs, which are found in agriculture, in horticulture, in animal breeding, in forests, in gardens and leisure facilities, in the protection of stored products and materials, and in the hygiene sector. They can preferably be employed as plant protection agents. They are active against normally sensitive and resistant species and against all or individual developmental stages.

They have a very broad insecticidal spectrum of action, in particular against the following animal pests:

From the order of the Anoplura (Phthiraptera), for example *Damalinia* spp., *Haematopinus* spp., *Linognathus* spp., *Pediculus* spp., *Trichodectes* spp.

From the class of the Arachnida, for example *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vacates lycopersici.*

From the class of the Bivalva, for example *Dreissena* spp.

From the order of the Chilopoda, for example *Geophilus* spp., *Scutigera* spp.

From the order of the Coleoptera, for example *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zea-landica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example *Onychiurus armatus.*

From the order of the Dermaptera, for example *Forficula auricularia.*

From the order of the Diplopoda, for example *Blaniulus guttulatus.*

From the order of the Diptera, for example *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

From the class of the Gastropoda, for example *Anion* spp., *Biomphalaria* spp., *Bulinus* spp., *Deroceras* spp., *Galba* spp., *Lymnaea* spp., *Oncomelania* spp., *Succinea* spp.

From the class of the helminths, for example *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

Protozoans, such as Eimeria, can also be controlled.

From the order of the Heteroptera, for example *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

From the order of the Homoptera, for example *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachy-*

*caudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus* arundinis, *Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistras, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

From the order of the Hymenoptera, for example *Diprion* spp., *Hoplocampa* spp., *Lasius* spp., *Monomorium pharaonis, Vespa* spp.

From the order of the Isopoda, for example *Armadillidium vulgare, Oniscus asellus, Porcellio scaber.*

From the order of the Isoptera, for example *Reticulitermes* spp., *Odontotermes* spp.

From the order of the Lepidoptera, for example *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

From the order of the Orthoptera, for example *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

From the order of the Siphonaptera, for example *Ceratophyllus* spp., *Xenopsylla cheopis.*

From the order of the Symphyla, for example *Scutigerella immaculata.*

From the order of the Thysanoptera, for example *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

From the order of the Thysanura, for example *Lepisma saccharina.*

The plant-parasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

It has been found that the use according to the invention of the active substance combinations demonstrates a potent insecticidal activity against insects which destroys industrial materials.

The following insects may be mentioned by way of example and by preference, but not by limitation:

Beetles such as *Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec., *Dinoderus minutus.*

Hymenoptera such as *Sirex juvencus, Urocerus gigas, Urocerus gigas taignus, Urocerus augur.*

Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails such as *Lepisma saccharina.*

Industrial materials are understood as meaning, in the present context, non-live materials such as, preferably, polymers, adhesives, glues, paper and board, leather, wood, derived timber products and paints.

The material to be protected from infestation with insects is very especially preferably timber and derived timber products.

Timber and derived timber products which can be protected by the active substance combinations according to the invention are to be understood as meaning by way of example: structural timber, wooden beams, railway sleepers, components of bridges, jetties, vehicles made of wood, boxes, pallets, containers, telegraph poles, wooden lagging, windows and doors made of wood, plywood, chipboard, joinery or wooden products which are used, quite generally, for building houses or in building joinery.

The active substance combinations can be used as such, in the form of concentrates or generally customary formulations such as powder, granules, solutions, suspensions, emulsions or pastes.

The abovementioned formulations can be prepared in a manner known per se, for example by mixing the active substances with at least one solvent, diluent, emulsifier, dispersant and/or binder or fixative, water repellent, optionally desiccants and UV stabilizers and, if appropriate, colorants and pigments as well as further processing aids.

The insecticidal active substance combinations or concentrates which are used for the protection of timber and derived timber products comprise the active substance according to the invention in a concentration of from 0.0001 to 95% by weight, in particular from 0.001 to 60% by weight.

The amount of the active substance combinations or concentrates employed depends on the species and the abundance of the insects and on the medium. Upon use, the optimal application rate can be determined in each case by a test series. However, in general it will suffice to employ from 0.0001 to 20% by weight, preferably from 0.001 to 10% by weight, of the active substance, based on the material to be protected.

The active substance combinations are also suitable for controlling animal pests, in particular insects, arachnids and mites, which are found in enclosed spaces such as, for example, dwellings, factory halls, offices, drivers' cabins and the like. To control these pests they can be used in insecticidal products for domestic premises. They are active against sensitive and resistant species and against all developmental stages. These pests include:

From the order of the Scorpionidea, for example *Buthus occitanus*.

From the order of the Acarina, for example *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example Avicularidae, Araneidae.

From the order of the Opiliones, for example *Pseudoscorpiones chelifer, Pseudoscorpiones cheiridium, Opiliones phalangium*.

From the order of the Isopoda, for example *Oniscus asellus, Porcellio scaber*.

From the order of the Diplopoda, for example *Blaniulus guttulatus, Polydesmus* spp. From the order of the Chilopoda, for example *Geophilus* spp.

From the order of the Zygentoma, for example *Ctenolepisma* spp., *Lepisma saccharina, Lepismodes inquilinus*.

From the order of the Blattaria, for example *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example *Acheta domesticus*.

From the order of the Dermaptera, for example *Forficula auricularia*.

From the order of the Isoptera, for example *Kalotermes* spp., *Reticulitermes* spp.

From the order of the Psocoptera, for example *Lepinatus* spp., *Liposcelis* spp.

From the order of the Coleoptera, for example *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example *Achroia grisella, Galleria mellonella, Plodia interpunctella, Tinea cloacella, Tinea pellionella, Tineola bisselliella*.

From the order of the Siphonaptera, for example *Ctenocephalides canis, Ctenocephalides felis, Pulex irritans, Tunga penetrans, Xenopsylla cheopis*.

From the order of the Hymenoptera, for example *Camponotus herculeanus, Lasius fuliginosus, Lasius niger, Lasius umbratus, Monomorium pharaonis, Paravespula* spp., *Tetramorium caespitum*.

From the order of the Anoplura, for example *Pediculus humanus capitis, Pediculus humanus corporis, Phthirus pubis*.

From the order of the Heteroptera, for example *Cimex hemipterus, Cimex lectularius, Rhodinus prolixus, Triatoma infestans*.

The application is carried out in aerosols, unpressurized sprays, for example pump sprays and atomizer sprays, automatic misting devices, foggers, foams, gels, vaporizer products with vaporizer platelets made of cellulose or polymer, liquid vaporizers, gel and membrane vaporizers, propeller-driven vaporizers, vaporization systems which do not consume energy (passive vaporization systems), moth papers, moth sachets and moth gels in the form of granules or dusts, in baits for scattering or bait stations.

The active substance combinations according to the invention are not only active against plant pests, hygiene pests and stored-product pests, but also, in the sector of veterinary medicine, against animal parasites (ectoparasites) such as hard ticks, soft ticks, scab mites, harvest mites, flies (stinging and licking), parasitic fly larvae, lice, hair lice, bird lice and fleas. These parasites include:

From the order of the Anoplurida, for example *Haematopinus* spp., *Linognathus* spp., *Pediculus* spp., *Phtirus* spp., *Solenopotes* spp.

From the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example *Pulex* spp., *Ctenocephalides* spp., *Xenopsylla* spp., *Ceratophyllus* spp.

From the order of the Heteropterida, for example *Cimex* spp., *Triatoma* spp., *Rhodnius* spp., *Panstrongylus* spp.

From the order of the Blattarida, for example *Blatta orientalis, Periplaneta americana, Blattela germanica, Supella* spp.

From the subclass of the Acari (Acarida) and the orders of the Meta- and Mesostigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active substance combinations according to the invention are also suitable for controlling arthropods which attack agricultural livestock such as, for example, cattle, sheep, goats, horses, pigs, donkeys, camels, buffaloes, rabbits, chickens, turkeys, ducks, geese, honeybees, other domestic animals such as, for example, dogs, cats, cage birds, aquarium fish and what are known as experimental animals such as, for example, hamsters, guinea pigs, rats and mice. By controlling these arthropods, it is intended to reduce deaths and performance reductions (in the case of meat, milk, wool, hides, eggs, honey and the like), so that more economical and simpler animal keeping is made possible by the use of the active substance combinations according to the invention.

In the veterinary sector, the active substance combinations according to the invention are applied in the known manner by enteral administration in the form of, for example, tablets, capsules, drinks, drenches, granules, pastes, boluses, the feed-through method, suppositories, by parenteral administration, such as, for example, by injections (intramuscular, subcutaneous, intravenous, intraperitoneal and the like), implants, by nasal application, by dermal application in the form of, for example, bathing or dipping, spraying, pouring-on and spotting-on, washing, dusting, and with the aid of active-substance-comprising shaped articles such as collars, ear tags, tail tags, limb bands, halters, marking devices and the like.

When used for livestock, poultry, domestic animals and the like, the active substance combinations can be applied as formulations (for example powders, emulsions, flowables) which comprise the active substances in an amount of from 1 to 80% by weight, either directly or after 100- to 10 000-fold dilution, or else as a chemical bath.

In certain concentrations, or at certain application rates, the active substance combinations according to the invention can, if appropriate, also be used as herbicides, safeners, growth regulators or agents for improving the plant characteristics, or as microbicides, for example as fungicides, antimycotics, bactericides, virucides (including as agents against viroids) or as agents against MLOs (mycoplasma-like organisms) and RLOs (rickettsia-like organisms).

The active substances can be converted into the customary formulations, such as solutions, emulsions, wettable powders, water- and oil-based suspensions, powders, dusts, pastes, soluble powders, soluble granules, granules for broadcasting, suspension emulsion concentrates, natural materials impregnated with active substance, synthetic materials impregnated with active substance, fertilizers and microencapsulations in polymeric materials.

These formulations are produced in a known manner, for example by mixing the active substances with extenders, that is to say liquid solvents and/or solid carriers, optionally with the use of surface-active agents, that is to say emulsifiers and/or dispersants and/or foam formers. The formulations are prepared either in suitable plants or else before or during application.

Adjuvants which may be used are those substances which are capable of imparting, to the composition itself and/or to preparations derived therefrom (for example spray mixtures, seed dressings), specific properties such as certain technical properties and/or also specific biological properties. Typical adjuvants which are suitable are: extenders, solvents and carriers.

Suitable extenders are, for example, water, polar and unpolar organic chemical fluids, for example from the classes of the aromatic and nonaromatic hydrocarbons (for example paraffins, alkylbenzenes, alkylnaphthalenes, chlorobenzenes), of the alcohols and polyols (which may optionally also be substituted, etherified and/or esterified), of the ketones (such as acetone, cyclohexanone), esters (including fats and oils) and (poly)ethers, of the unsubstituted and substituted amines, amides, lactams (such as N-alkylpyrrolidones) and lactones, of the sulphones and sulphoxides (such as dimethyl sulphoxide).

If water is used as the extender, cosolvents may also be used, for example organic solvents. Liquid solvents which are suitable are essentially: aromatics such as xylene, toluene or alkylnaphthalenes, chlorinated aromatics, or chlorinated aliphatic hydrocarbons, such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents, such as dimethyl sulphoxide, and water.

In accordance with the invention, carrier means a natural or synthetic, organic or inorganic substance which may be solid or liquid and with which the active substances are mixed or to which the active substances are bound in order to improve their use properties, in particular for application to plants or plant parts or seed. In general, the solid or liquid carrier is inert, and it should be capable of being used in agriculture. Suitable Solid or Liquid Carriers are:

for example ammonium salts and ground natural minerals, such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and synthetic granules of inorganic and organic meals, and granules of organic material such as paper, sawdust, coconut shells, maize cobs and tobacco stalks; suitable emulsifiers and/or foam formers are: for example non-ionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: non-ionic and/or ionic substances, for example from the classes of the alcohol-POE and/or -POP ethers, acid and/or POP-POE esters, alkylaryl and/or POP-POE ethers, fatty and/or POP-POE adducts, POE- and/or POP-polyol derivatives, POE- and/or POP-sorbitan or -sugar adducts, alkyl sulphates or aryl sulphates, alkylsulphonates or arylsulphonates and alkyl phosphates or aryl phosphates, or the corresponding PO-ether adducts. Furthermore suitable are oligo- or polymers, for example those derived from vinylic monomers, from acrylic acid, from EO and/or from PO alone or in combination with, for example, (poly)alcohols or (poly)amines. It is also possible to employ lignin and its sulphonic acid derivatives, unmodified and modified celluloses, aromatic and/or aliphatic sulphonic acids, and their adducts with formaldehyde.

Tackifiers such as carboxymethylcellulose, natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanin dyestuffs, and trace nutrients such as salts of iron, manganese, boron, copper, cobalt, molybdenum and zinc.

Other possible additives are fragrances, mineral or vegetable, optionally modified, oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve the chemical and/or physical stability may also be present.

The active substance content of the use forms prepared from the commercially available formulations can vary within wide ranges. The active substance concentration of the use forms is in the range of from 0.00000001 to 97% by weight of active substance, preferably in the range of from 0.0000001 to 97% by weight, especially preferably in the range of from 0.000001 to 83% by weight or 0.000001 to 5% by weight and very especially preferably in the range of from 0.0001 to 1% by weight.

The active substance combinations can be used in their commercially available formulations and in the use forms prepared from these formulations as a mixture with further active substances such as attractants, sterilants, bactericides, nematicides, growth regulators, herbicides, safeners, fertilizers or semiochemicals.

A mixture with other known active substances such as herbicides, fertilizers, growth regulators, safeners, semiochemicals, or else with agents for improving the plant properties, is also possible.

When used as insecticides according to the invention, the use of the active substance combinations, in their commercially available formulations and in the use forms prepared from these formulations, may furthermore be effected as a mixture with synergists. Synergists are compounds by which the activity of the active substances is increased without it being necessary for the synergist added to be active itself.

When used as insecticides, the active substance combinations according to the invention, in their commercially available formulations and in the use forms prepared from these formulations, may furthermore be present as a mixture with inhibitors which reduce, after application, the degradation of the active substance in the environment of the plant, on the surface of plant parts or in plant tissues.

The application is effected in a customary manner adapted to suit the use forms.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example fruits, seeds, cuttings, tubers, rhizomes, slips, seeds, bulblets, offshoots and runners.

The treatment according to the invention of the plants and plant parts with the active substance combinations is effected directly or by acting on their environment, habitat or store room by the customary treatment methods, for example by dipping, spraying, vaporizing, atomizing, scattering, painting on, injecting and, in the case of propagation material, in particular in the case of seed, furthermore by coating with one or more coats. In this context, the active substance combinations can be prepared before the treatment by mixing the individual active substances. Another possibility is that the treatment is effected in succession by first using the compound (A) of the formula (I) followed by treatment with an active substance from groups (2) to (8). However, it is also possible to first treat the plants or plant parts with an active substance from groups (2) to (8), followed by treatment with the compound (A) of the formula (I).

Plants which can be treated in accordance with the invention and which may be mentioned are the following: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., Actimidaceae sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes and potatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumbers), *Alliaceae* sp. (for example leeks, onions), *Papilionaceae* sp. (for example peas, soy beans); major crop plants such as *Gramineae* sp. (for example maize, turf, cereals such as wheat, rye, rice, barley, oats, millet/sorghum and triticale), *Asteraceae* sp. (for example sunflower), *Brassicaceae* sp. (for example white cabbage, red cabbage, broccoli, cauliflower, Brussels sprouts, pal choi, kohlrabi, small radishes, and also oilseed rape, mustard, horseradish and cress), *Fabacae* sp. (for example beans, peanuts), *Chenopodiaceae* sp. (for example sugar beet, fodder beet, swiss chard, beetroot); useful plants and ornamentals in gardens and forests; and in each case genetically modified types of these plants.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example, antisense technology, cosuppression technology or RNA interference—RNAi—technology). A heterologous gene that is located in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products are possible, which exceed the effects which were actually to be expected.

At certain application rates, the active compound combinations according to the invention may also have a strengthening effect in plants. Accordingly, they are also suitable for mobilizing the defence system of the plant against attack by unwanted phytopathogenic fungi and/or microorganisms and/or viruses. This may, if appropriate, be one of the reasons of the enhanced activity of the combinations according to the invention, for example against fungi. Plant-strengthening (resistance-inducing) substances are to be understood as meaning, in the present context, those substances or combinations of substances which are capable of stimulating the defence system of plants in such a way that, when subsequently inoculated with unwanted phytopathogenic fungi and/or microorganisms and/or viruses, the treated plants display a substantial degree of resistance to these unwanted phytopathogenic fungi and/or microorganisms and/or viruses. In the present case, unwanted phytopathogenic fungi and/or microorganisms and/or viruses are to be understood as meaning phytopathogenic fungi, bacteria and viruses. Thus, the substances according to the invention can be employed for protecting plants against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are preferably to be treated according to the invention include all plants which have genetic material which impart particularly advantageous, useful traits to these plants (whether obtained by breeding and/or biotechnological means).

Plants and plant cultivars which are also preferably to be treated according to the invention are resistant against one or more biotic stresses, i.e. said plants have a better defence against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses. Abiotic stress conditions may include, for example, drought, cold temperature exposure, heat exposure, osmotic stress, flooding, increased soil salinity, increased mineral exposure, ozone exposure, high light exposure, limited availability of nitrogen nutrients, limited availability of phosphorus nutrients or shade avoidance.

Plants and plant cultivars which may also be treated according to the invention, are those plants characterized by enhanced yield characteristics. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore by affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristic of heterosis or hybrid vigour which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g. in corn) be produced by detasseling, (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in the hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxido-reductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes.

Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase.

Further herbicide-tolerant plants are also plants that are made tolerant to the herbicides inhibiting the enzyme hydroxyphenylpyruvatedioxygenase (HPPD). Hydroxyphenylpyruvatedioxygenases are enzymes that catalyze the reaction in which parahydroxyphenylpyruvate (HPP) is transformed into homogentisate. Plants tolerant to HPPD-inhibitors can be transformed with a gene encoding a naturally-occurring resistant HPPD enzyme, or a gene encoding a mutated HPPD enzyme. Tolerance to HPPD-inhibitors can also be obtained by transforming plants with genes encoding certain enzymes enabling the formation of homogentisate despite the inhibition of the native HPPD enzyme by the HPPD-inhibitor. Tolerance of plants to HPPD inhibitors can also be improved by transforming plants with a gene encoding an enzyme prephenate dehydrogenase in addition to a gene encoding an HPPD-tolerant enzyme.

Still further herbicide resistant plants are plants that are made tolerant to acetolactate synthase (ALS) inhibitors. Known ALS-inhibitors include, for example, sulfonylurea, imidazolinone, triazolopyrimidines, pyrimidinyloxy(thio)benzoates, and/or sulfonylaminocarbonyltriazolinone herbicides. Different mutations in the ALS enzyme (also known as acetohydroxyacid synthase, AHAS) are known to confer tolerance to different herbicides and groups of herbicides. The production of sulfonylurea-tolerant plants and imidazolinone-tolerant plants has been described. Other imidazolinone-tolerant plants have also been described. Further sulfonylurea- and imidazolinone-tolerant plants have also been described.

Other plants tolerant to imidazolinone and/or sulfonylurea can be obtained by induced mutagenesis, selection in cell cultures in the presence of the herbicide or mutation breeding as described for example for soya beans, for rice, for sugar beet, for lettuce or for sunflower.

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

An "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins listed by Crickmore at al., Microbiology and Molecular Biology Reviews (1998), 62, 807-813, updated by Crickmore et al. (2005) in the *Bacillus thuringiensis* toxin nomenclature, online at: http://www.lifesci.sussex.ac.uk/Home/Neil_Crickmore/Bt/), or insecticidal portions thereof, e.g., proteins of the Cry protein classes Cry1Ab, Cry1Ac, Cry1F, Cry2Ab, Cry3Ae, or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, e.g. the Cry1A.105 protein produced by corn event MON98034; or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation, such as the Cry3Bb1 protein in corn events MON863 or MON88017, or the Cry3A protein in corn event MIR604; or
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, e.g., proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1a and VIP2A proteins; or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes induced into the encoding DNA during cloning or transformation (while still encoding an insecticidal protein), such as the VIP3Aa protein in cotton event COT102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant cultivars (obtained by plant biotechnology methods such as genetic engineering) which may also be treated according to the invention are tolerant to abiotic stresses. Such plants can be obtained by genetic transformation, or by selection of plants containing a mutation imparting such stress resistance. Particularly useful stress tolerance plants include:
a. plants which contain a transgene capable of reducing the expression and/or the activity of poly(ADP-ribose)polymerase (PARP) gene in the plant cells or plants.
b. plants which contain a stress tolerance enhancing transgene capable of reducing the expression and/or the activity of the PARG encoding genes of the plants or plants cells.
c. plants which contain a stress tolerance enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyl transferase, nicotinamide adenine dinucleotide synthetase or nicotine amide phosphoribosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) transgenic plants which synthesize a modified starch, which in its physical-chemical characteristics, in particular the amylose content or the amylose/amylopectin ratio, the degree of branching, the average chain length, the side chain distribution, the viscosity behaviour, the gelling strength, the starch grain size and/or the starch grain morphology, is changed in comparison with the synthesized starch in wild type plant cells or plants, so that this modified starch is better suited for special applications. Said transgenic plants synthesizing a modified starch have been described.
2) transgenic plants which synthesize non-starch carbohydrate polymers or which synthesize non starch carbohydrate polymers with altered properties in comparison to wild type plants without genetic modification. Examples are plants which produce polyfructose, especially of the inulin and levan-type, plants which produce alpha-1,4-glucans, plants which produce alpha-1,6 branched alpha-1,4-glucans, and plants producing alternan.
3) transgenic plants which produce hyaluronan.

Plants or plant cultivars (that can be obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants which contain an altered form of cellulose synthase genes;
b) plants, such as cotton plants which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, e.g. through downregulation of fibre-selective β-1,3-glucanase;
f) plants, such as cotton plants, which have fibres with altered reactivity, e.g. through the expression of N-acetylglucosaminetransferase gene including nodC and chitin synthase genes.

Plants or plant cultivars (that can be obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plant such as oilseed rape plants, which produce oil having a low level of saturated fatty acids.

Particularly useful transgenic plants which may be treated according to the invention are plants which comprise one or more genes which encode one or more toxins, are the following which are sold under the trade names YIELD GARD® (for example maize, cotton, soya beans), KnockOut® (for example maize), BiteGard® (for example maize), Bt-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, that are listed for example in the databases for various national or regional regulatory agencies (see for example http://gmoinfo.jrc.it/gmp_browse.aspx and http://www.agbios.com/dbase.php).

The active substance combinations according to the invention are particularly suitable for the treatment of seed. The combinations according to the invention which have been mentioned above as being preferred or especially preferred must be mentioned by preference in this context. Thus, a large proportion of the damage to crop plants which is caused by pests is already generated by infestation of the seed while the seed is stored and after the seed is introduced into the soil, and during and immediately after germination of the plants. This phase is particularly critical since the roots and shoots of the growing plant are particularly sensitive and even a small amount of damage can lead to the death of the whole plant. There is therefore in particular a great interest in protecting the seed and the germinating plant by using suitable compositions.

The control of pests by treating the seed of plants has been known for a long time and is the subject of continuous improvements. However, the treatment of seed poses a series of problems which cannot always be solved in a satisfactory manner. Thus, it is desirable to develop methods of protecting the seed and the germinating plant which dispense with the additional application of plant protection compositions after sowing or after the emergence of the plants. It is furthermore desirable to optimize the amount of the active substance employed in such a way as to provide the best possible protection for the seed and the germinating plant against attack by pests without, however, damaging the plant itself by the active substance employed. In particular, methods for the treatment of seed should also include the intrinsic fungicidal and/or insecticidal properties of transgenic plants in order to achieve an optimal protection of the seed and of the germinating plant while keeping the application rate of plant protection compositions as low as possible.

The present invention therefore particularly also relates to a method of protecting seed and germinating plants from attack by pests by treating the seed with an active substance combination according to the invention. The method according to the invention for protecting seed and germinating plants from attack by pests comprises a method in which the seed is treated simultaneously with the compound (A) of the formula (I) and an active substance from the abovementioned groups (2) to (8). It also comprises a method in which the seed is treated at different times with a compound of the formula (I) and an active substance from the abovementioned groups (2) to (8).

The invention likewise relates to the use of the active substance combinations according to the invention for the treatment of seed for protecting the seed and the germinating plant from animal pests.

The invention furthermore relates to seed which has been treated with an active substance combination according to the invention as a protection from pests. The invention also relates to seed which has been treated simultaneously with a compound of the formula (I) and an active substance from the abovementioned groups (2) to (8). The invention furthermore relates to seed which has been treated at different times with a compound of the formula (I) and an active substance from the abovementioned groups (2) to (8). In the case of seed which has been treated at different times with a compound of the formula (I) and an active substance from the abovementioned groups (2) to (8), the individual active substances of the active substance combination according to the invention may be present on the seed in different layers. In this context, the layers which contain a compound of the formula (I) and an active substance from the abovementioned groups (2) to (8) may, if appropriate, be separated by an intermediate layer. The invention also relates to seed where a compound of the formula (I) and an active substance from the abovementioned groups (2) to (25) are applied as component of a coat or as further layer(s) in addition to a coat.

One of the advantages of the present invention is that, owing to the particular systemic properties of the active substance combinations according to the invention, the treatment of the seed with these active substance combinations does not only protect the seed itself from animal pests, but also the plants which it gives rise to, after they have emerged. In this manner, the immediate treatment of the crop at the point in time of sowing or shortly thereafter can be dispensed with.

A further advantage is the synergistic increase of the insecticidal activity of the active substance combinations according to the invention in comparison with the individual insecticidal active substance, which exceeds the activity to be expected when the two active substances are employed individually. This makes possible an optimization of the amount of the active substances employed.

The fact that the active substance combinations according to the invention can also be employed in particular in transgenic seed, is also considered advantageous.

The active substance combinations according to the invention are suitable for the protection of seed of any plant variety as already mentioned above which is employed in agriculture, in the greenhouse, in forests or in horticulture. In particular, this takes the form of seed of maize, peanut, canola, oilseed rape, poppy, soya, cotton, beet (for example sugar beet and fodder beet), rice, sorghum/millet, wheat, barley, oats, rye, triticale, sunflower, tobacco, potatoes or vegetables (for example tomatoes, brassicas). The active substance combinations according to the invention are also suitable for the treatment of the seed of fruit plants and vegetables as already mentioned above. Particularly important is the treatment of the seed of rice, barley, oats, rye, triticale, maize, soya, cotton, wheat and canola or oilseed rape.

Within the scope of the present invention, the active substance combination according to the invention is applied to the seed either alone or in the form of a suitable formulation. The seed is preferably treated in a state in which it is sufficiently stable to avoid damage during the treatment. In general, treatment of the seed can be effected at any point in time between harvest and sowing. Usually, seed is used which has been separated from the plant and freed from cobs, hulls, stems, coats, hair or pulp. Thus, it is possible, for example, to use seed which has been harvested, cleaned and dried down to a moisture content of below 15% by weight. Alternatively, seed may be used which has been dried, then treated with water, for example, and then redried.

When treating seed, care must be taken generally that the amount of the active substance combination according to the invention and/or further additives which is/are applied to the seed is chosen in such a way that the germination of the seed is not adversely affected, or the plant which the seed gives rise to is not damaged. This is in particular the case for active substances which may have phytotoxic effects at certain application rates.

The compositions according to the invention can be applied directly, which means without comprising further components and without having been diluted. As a rule, it is preferable to apply the compositions to the seed in the form of a suitable formulation. Suitable formulations and methods for the treatment of seed are known to the skilled worker and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active substances which can be used according to the invention can be converted into the customary seed-dressing product formulations such as solutions, emulsions, suspensions, powders, foams, slurries and other coating compositions for seed, and ULV formulations.

These formulations are prepared in the known manner by mixing the active substances with customary additives such as, for example, customary extenders and also solvents or diluents, colorants, wetters, dispersants, emulsifiers, antifoams, preservatives, secondary thickeners, adhesives, gibberellins, and also water.

Colorants which may be present in the seed-dressing product formulations which can be used according to the invention are all colorants which are customary for such purposes. Both pigments, which are sparingly soluble in water, and dyes, which are soluble in water, may be used. Examples of colorants which may be mentioned are those known by the names Rhodamin B, C.I. Pigment Red 112 and C.I. Solvent Red 1.

Wetters which may be present in the seed-dressing product formulations which can be used according to the invention are all substances which are conventionally used for the formulation of agrochemical active substances and for promoting wetting. Alkylnaphthalenesulphonates, such as diisopropyl- or diisobutylnaphthalenesulphonates, can preferably be used.

Suitable dispersants and/or emulsifiers which may be present in the seed-dressing product formulations which can be used in accordance with the invention are all non-ionic, anionic and cationic dispersants which are conventionally used for the formulation of agrochemical active substances. Non-ionic or anionic dispersants or mixtures of non-ionic or anionic dispersants can preferably be used. Suitable non-ionic dispersants which may be mentioned are, in particular, ethylene oxide/propylene oxide block polymers, alkylphenol polyglycol ethers and tristryrylphenol polyglycol ethers, and their phosphated or sulphated derivatives. Suitable anionic dispersants are, in particular, lignosulphonates, polyacrylic acid salts and arylsulphonate/formaldehyde condensates.

Antifoams which may be present in the seed-dressing product formulations which can be used according to the invention are all foam-suppressing substances conventionally used for the formulation of agrochemical active substances. Silicone antifoams and magnesium stearate can preferably be used.

Preservatives which may be present in the seed-dressing product formulations which can be used according to the invention are all substances which can be employed in agrochemical compositions for such purposes. Examples which may be mentioned are dichlorophene and benzyl alcohol hemiformal.

Secondary thickeners which may be present in the seed-dressing product formulations which can be used according to the invention are all substances which can be employed in agrochemical compositions for such purposes. Cellulose derivatives, acrylic acid derivatives, xanthan, modified clays and highly disperse silica are preferably suitable.

Adhesives which may be present in the seed-dressing product formulations which can be used according to the invention are all customary binders which can be employed in seed-dressing products. Polyvinylpyrrolidone, polyvinyl acetate, polyvinyl alcohol and tylose may be mentioned by preference.

Gibberellins which may be present in the seed-dressing product formulations which can be used according to the invention are preferably the gibberellins A1, A3 (=gibberellic acid), A4 and A7, with gibberellic acid being particularly preferably used. The gibberellins are known (cf. R. Wegler "Chemie der Pflanzenschutz- and Schädlingsbekämpfungs-mittel" [Chemistry of Plant Protectants and Pesticides], Vol. 2, Springer Verlag, 1970, pp. 401-412).

The seed-dressing product formulations which can be used in accordance with the invention can be employed either directly or after previous dilution with water for the treatment of a wide range of seeds, including the seed of transgenic plants. In this context, additional synergistic effects may also occur as a consequence of the interaction with the substances formed by expression.

Suitable apparatuses which can be employed for treating seed with the seed-dressing product formulations which can be used in accordance with the invention, or with the preparations prepared therefrom by addition of water, are all mixing apparatuses which can usually be employed for dressing seed. Specifically, a seed-dressing procedure is followed in which the seed is placed in a mixer, the amount of seed-dressing product formulation desired in each case is added, either as such or after previously diluting it with water, and the contents of the mixer are mixed until the formulation has been distributed uniformly on the seed. If appropriate, this is followed by a drying process.

The active substance combinations according to the invention are also suitable for increasing the yield. Moreover, their toxicity is low, and they are well tolerated by plants.

The active substance combinations according to the invention also display a potent strengthening action in plants. They are therefore suitable for mobilizing the plants' intrinsic defences against attack by undesired microorganisms.

Plant-strengthening (resistance-inducing) substances are to be understood as meaning, in the present context, those substances which are capable of stimulating the plant defence system in such a way that the treated plants, when subsequently inoculated with undesired microorganisms, show a large degree of resistance to these microorganisms.

The plants listed can be treated in a particularly advantageous manner with the active substance combinations according to the invention. The preferred ranges detailed above also apply to the treatment of these plants.

The good insecticidal activity of the active substance combinations according to the invention can be seen from the examples which follow. While the individual active substances show weaknesses in the insecticidal activity, the combinations demonstrate an activity which exceeds a simple sum of activities.

A synergistic effect in insecticides is always present when the insecticidal activity of the active substance combinations exceeds the total of the activities of the active substances applied individually.

The activity to be expected for a given combination of two active substances can be calculated as follows (cf. Colby, S. R., "Calculating Synergistic and Antagonistic Responses of Herbicide Combinations", Weeds 15, pages 20-22, 1967):

If
X means the degree of destruction expressed in % of the untreated control when using active substance A at an application rate of $\underline{m}$ ppm or m g/ha,
Y means the degree of destruction expressed in % of the untreated control when using active substance B at an application rate of $\underline{n}$ ppm or n g/ha, and
E means the degree of destruction expressed in % of the untreated control when employing active substances A and B at application rates of $\underline{m}$ and $\underline{n}$ ppm or m and n g/ha,
then $$E = X + Y - \frac{X \times Y}{100}$$

If the actual insecticidal degree of destruction is greater than calculated, the combination is superadditive regarding its destruction, i.e. a synergistic effect is present. In this case, the degree of destruction which is actually observed must exceed the value calculated on the basis of the above formula for the expected degree of destruction (E).

EXAMPLE A

*Myzus persicae* Test

Solvent: 7 parts by weight of dimethylformamide
Emulsifier: 2 parts by weight of alkylaryl polyglycol ether To prepare a suitable preparation of active substance, 1 part by weight of active substance is mixed with the stated amounts of solvent and emulsifier, and the concentrate is diluted to the desired concentration with emulsifier-containing water.

Cabbage leaves (*Brassica oleracea*) which are severely infested with the green peach aphid (*Myzus persicae*) are treated by being dipped into the active substance preparation of the desired concentration.

After the desired period of time, the destruction is determined in %. Here, 100% means that all the aphids have been destroyed; 0% means that no aphids have been destroyed. The destruction rates which have been determined are entered in the Colby formula (see sheet 1).

In this test, a synergistically increased activity in comparison with the active substances applied individually is demonstrated for example by the following active substance combinations according to the present application:

TABLE A1

Plant-injurious insects
*Myzus persicae* test

| Active substance | Concentration in ppm | Destruction in % after 6 d | |
|---|---|---|---|
| | | found* | calc.** |
| Isotianil | 500 | 10 | |
| clothianidin | 0.8 | 55 | |
| Isotianil + clothianidin (625:1) according to the invention | 500 + 0.8 | 95 | 59.5 |

*found = found activity;
**calc. = activity calculated with the Colby formula

TABLE A2

Plant-injurious insects
*Myzus persicae* test

| Active substance | Concentration in ppm | Destruction in % after 6 d | |
|---|---|---|---|
| Isotianil | 500 | 0 | |
| Thiacloprid | 0.8 | 45 | |
| | | found* | calc.** |
| Isotianil + thiacloprid (625:1) according to the invention | 500 + 0.8 | 95 | 45 |
| Imidacloprid | 0.8 | 75 | |
| | | found* | calc.** |
| Isotianil + imidacloprid (625:1) according to the invention | 500 + 0.8 | 95 | 75 |
| Fipronil | 100 | 65 | |
| | | found* | calc.** |
| Isotianil + fipronil (5:1) according to the invention | 500 + 100 | 80 | 65 |

*found = found activity;
**calc. = activity calculated with the Colby formula

TABLE A3

Plant-injurious insects
*Myzus persicae* test

| Active substance | Concentration in ppm | Destruction in % after 1 d | |
|---|---|---|---|
| Isotianil | 500 | 0 | |
| Thiamethoxam | 0.8 | 75 | |
| | | found* | calc.** |
| Isotianil + thiamethoxam (625:1) according to the invention | 500 + 0.8 | 90 | 75 |

*found = found activity;
**calc. = activity calculated with the Colby formula

EXAMPLE B

Phaedon Cochleariae Larvae Test

Solvent: 7 parts by weight of dimethylformamide

Emulsifier: 2 parts by weight of alkylaryl polyglycol ether

To prepare a suitable preparation of active substance, 1 part by weight of active substance is mixed with the stated amounts of solvent and emulsifier, and the concentrate is diluted to the desired concentration with emulsifier-containing water.

Cabbage leaves (*Brassica oleracea*) are treated by being dipped into the active substance preparation of the desired concentration and are populated with mustard beetle larvae (*Phaedon cochleariae*) while the leaves are still moist.

After the desired period of time, the destruction is determined in %. Here, 100% means that all the beetle larvae have been destroyed; 0% means that no beetle larvae have been destroyed. The destruction rates which have been determined are entered in the Colby formula (see sheet 1).

In this test, a synergistically increased activity in comparison with the active substances applied individually is demonstrated for example by the following active substance combinations according to the present application:

TABLE B1

Plant-injurious insects
*Phaedon cochleariae* larvae test

| Active substance | Concentration in ppm | Destruction in % after 6 d | |
|---|---|---|---|
| Isotianil | 500 | 0 | |
| Clothianidin | 4 | 65 | |
| | | found* | calc.** |
| Isotianil + clothianidin (125:1) according to the invention | 500 + 4 | 75 | 65 |
| Thiacloprid | 4 | 0 | |
| | | found* | calc.** |
| Isotianil + thiacloprid (125:1) according to the invention | 500 + 4 | 30 | 0 |
| Imidacloprid | 20 | 75 | |
| | | found* | calc.** |
| Isotianil + imidacloprid (25:1) according to the invention | 500 + 20 | 100 | 75 |
| Thiamethoxam | 20 | 80 | |
| | | found* | calc.** |
| Isotianil + thiamethoxam (25:1) according to the invention | 500 + 20 | 100 | 80 |

*found = found activity;
**calc. = activity calculated with the Colby formula

EXAMPLE C

*Plutella*-Xylostella Test (Sensitive Strain)

Solvent: 7 parts by weight of dimethylformamide

Emulsifier: 2 parts by weight of alkylaryl polyglycol ether

To prepare a suitable preparation of active substance, 1 part by weight of active substance is mixed with the stated amounts of solvent and emulsifier, and the concentrate is diluted to the desired concentration with emulsifier-containing water.

Cabbage leaves (*Brassica oleracea*) are treated by being dipped into the active substance preparation of the desired concentration and are populated with diamondback moth caterpillars (*Plutella xylostella*, sensitive strain) while the leaves are still moist.

After the desired period of time, the destruction is determined in %. Here, 100% means that all the caterpillars have been destroyed; 0% means that no caterpillars have been destroyed. The destruction rates which have been determined are entered in the Colby formula (see sheet 1).

In this test, a synergistically increased activity in comparison with the active substances applied individually is demonstrated for example by the following active substance combinations according to the present application:

TABLE C1

Plant-injurious insects
*Plutella xylostella* (normally-sensitive) test

| Active substance | Concentration in ppm | Destruction in % after 6 d | |
|---|---|---|---|
| Isotianil | 500 | 0 | |
| Clothianidin | 20 | 25 | |
| | | found* | calc.** |
| Isotianil + clothianidin (25:1) according to the invention | 500 + 20 | 75 | 25 |
| Thiacloprid known | 20 | 45 | |
| | | found* | calc.** |
| Isotianil + thiacloprid (25:1) according to the invention | 500 + 20 | 65 | 45 |

*found = found activity;
**calc. = activity calculated with the Colby formula

EXAMPLE D

*Spodoptera frugiperda* Test

Solvent: 7 parts by weight of dimethylformamide

Emulsifier: 2 parts by weight of alkylaryl polyglycol ether

To prepare a suitable preparation of active substance, 1 part by weight of active substance is mixed with the stated amounts of solvent and emulsifier, and the concentrate is diluted to the desired concentration with emulsifier-containing water.

Cabbage leaves (*Brassica oleracea*) are treated by being dipped into the active substance preparation of the desired concentration and are populated with armyworm caterpillars (*Spodoptera frugiperda*) while the leaves are still moist.

After the desired period of time, the destruction is determined in %. Here, 100% means that all the caterpillars have been destroyed; 0% means that no caterpillars have been destroyed. The destruction rates which have been determined are entered in the Colby formula (see sheet 1).

In this test, a synergistically increased activity in comparison with the active substances applied individually is demonstrated for example by the following active substance combinations according to the present application:

TABLE D1

Plant-injurious insects
*Spodoptera frugiperda* test

| Active substance | Concentration in ppm | Destruction in % after 3 d | |
|---|---|---|---|
| Isotianil | 500 | 10 | |
| Clothianidin | 4 | 95 | |
| | | found* | calc.** |
| Isotianil + clothianidin (125:1) according to the invention | 500 + 4 | 100 | 95.5 |

*found = found activity;
**calc. = activity calculated with the Colby formula

TABLE D2

Plant-injurious insects
*Spodoptera frugiperda* test

| Active substance | Concentration in ppm | Destruction in % after 6 d | |
|---|---|---|---|
| Isotianil | 500 | 20 | |
| Thiamethoxam | 20 | 70 | |
| | | found* | calc.** |
| Isotianil + thiamethoxam (25:1) according to the invention | 500 + 4 | 90 | 76 |

*found = found activity;
**calc. = activity calculated with the Colby formula

TABLE D3

Plant-injurious insects
*Spodoptera frugiperda* test

| Active substance | Concentration in ppm | Destruction in % after 6 d | |
|---|---|---|---|
| Isotianil | 500 | 0 | |
| Fipronil | 0.8 | 5 | |
| | | found* | calc.** |
| Isotianil + fipronil (625:1) according to the invention | 500 + 0.8 | 25 | 5 |

*found = found activity;
**calc. = activity calculated with the Colby formula

The invention claimed is:

1. A method of controlling animal pests comprising applying to an animal pest a composition consisting of synergistically effective amounts of:

(I) 3,4-dichloro-2'-cyano-1,2-thiazole-5-carboxanilide (isotianil) of formula I:

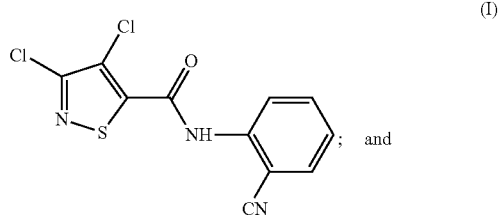 [SMILES: N#Cc1ccccc1NC(=O)c1snc(Cl)c1Cl]

(II) at least one active substance selected from the group consisting of:

(1) a neonicotinyl selected from the group consisting of

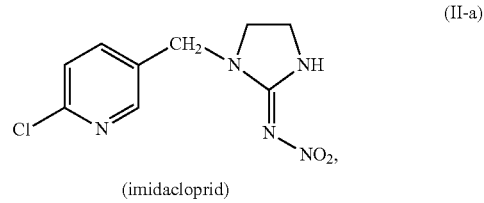

(imidacloprid)

(II-b)

(thiacloprid)

(II-c)

(thiamethoxam)

(II-d)

(clothianidin)

(2) a phenylpyrazole of formula IV:

(IV)

wherein R³ is —CF₃ (fipronil) or —C₂H₅ (ethiprole);
and extenders and/or surface active agents,
wherein the animal pest is from the order of Coleoptera, Lepidoptera, or Homoptera.

2. The method according to claim 1 wherein the at least one active substance is a neonicotinyl.

3. The method according to claim 2 wherein the neonicotinyl is imidacloprid.

4. The method according to claim 2 wherein the neonicotinyl is clothianidin.

5. The method according to claim 2 wherein the neonicotinyl is thiacloprid.

6. The method according to claim 2 wherein the neonicotinyl is thiamethoxam.

7. The method according to claim 1 wherein the at least one active substance is a phenylpyrazole.

8. The method according to claim 7 wherein the phenylpyrazole is fipronil.

9. The method according to claim 2 wherein the weight ratio of Isotianil
to the (1) neonicotinyl is between 1:0.001 and 1:1000, and
to the (2) phenylpyrazole is between 1:0.001 and 1:1000.

10. The method according to claim 1 wherein the animal pest is from the order of the Lepidoptera.

11. The method according to claim 1 wherein the animal pest is from the order of the Coleoptera.

12. The method according to claim 1 wherein the animal pest is from the order of the Homoptera.

13. The method according to claim 1, wherein the animal pest is *Myzus persicae*.

14. The method according to claim 1, wherein the animal pest is *Phaedon cochleariae*.

15. The method according to claim 13, wherein the at least one active substance is a neonicotinyl.

16. The method according to claim 14, wherein the neonicotinyl is imidacloprid.

17. The method according to claim 15, wherein the weight ratio of Isotianil to the neonicotinyl is between 1:0.001 and 1:1000.

18. A method of protecting a seed or a plant from which the seed grows from damage by animal pests comprising treating an animal pest with a composition consisting of synergistically effective amounts of:

(I) 3,4-dichloro-2'-cyano-1,2-thiazole-5-carboxanilide (isotianil) of formula I:

(I)

; and (II) at least one active substance selected from the group consisting of:
(1) a neonicotinyl selected from the group consisting of (II-a)

(imidacloprid)

(II-b)

(thiacloprid)

(II-c)

and (thiamethoxam)

(II-d)

(clothianidin)

(2) a phenylpyrazole of formula IV:

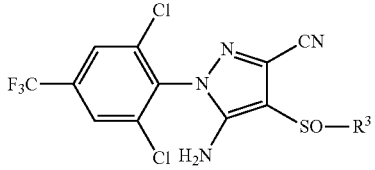

wherein $R^3$ is —$CF_3$ (fipronil) or —$C_2H_5$ (ethiprole);
and extenders and/or surface active agents,
wherein the animal pest is from the order of Coleoptera, Lepidoptera, or Homoptera.

19. The method according to claim 18 wherein the seed is transgenic seed.

20. The method according to claim 18, wherein the animal pest is *Myzus persicae*.

21. The method according to claim 18, wherein the animal pest is *Phaedon cochleariae*.

22. The method according to claim 18, wherein the animal pest is *Plutella xylostella*.

23. The method according to claim 18, wherein the animal pest is *Spodoptera frugiperda*.

24. The method according to claim 1, wherein the animal pest is *Plutella xylostella*.

25. The method according to claim 1, wherein the animal pest is *Spodoptera frugiperda*.

26. A composition comprising an active substance combination consisting of synergistically effective amounts of:
   (I) 3,4-dichloro-2'-cyano-1,2-thiazole-5-carboxanilide (isotianil) of formula I:

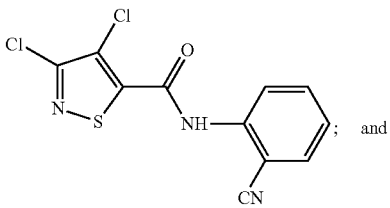

(II) at least one active substance selected from the group consisting of:
   (1) a neonicotinyl selected from the group consisting of

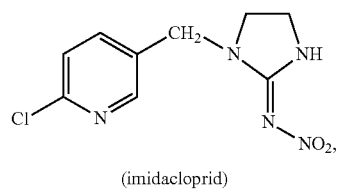

(imidacloprid)

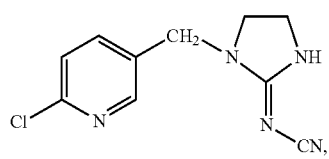

(thiacloprid)

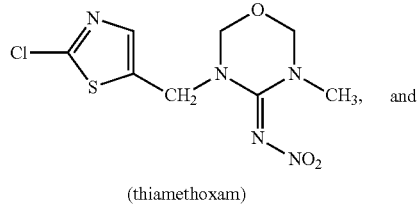

(thiamethoxam)

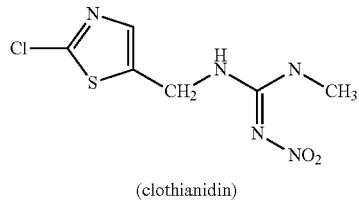

(clothianidin)

(2) a phenylpyrazole of formula IV:

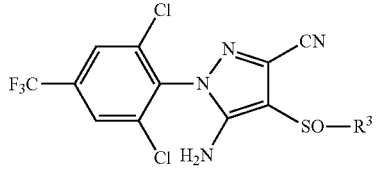

wherein $R^3$ is —$CF_3$ (fipronil) or —$C_2H_5$ (ethiprole);
and extenders and/or surface active agents, wherein the active substance combination is applied to an animal pest from the order of Coleoptera, Lepidoptera, and Homoptera; and wherein the active combination is synergistically effective in controlling said animal pest once applied thereto.

27. A method of protecting a plant or plant part in need of protection from animal pest damage, said method consisting of contacting an animal pest with a composition comprising synergistically effective amounts of:
   (I) 3,4-dichloro-2'-cyano-1,2-thiazole-5-carboxanilide (isotianil) of formula I:

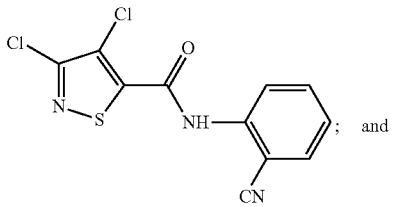

(II) at least one active substance selected from the group consisting of:
   (1) a neonicotinyl selected from the group consisting of

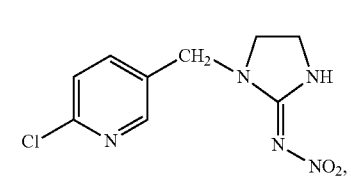

(imidacloprid)

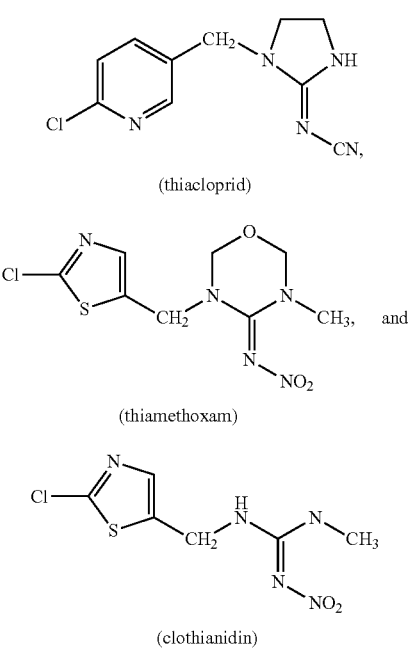

(thiacloprid)

(thiamethoxam)

(clothianidin)

(2) a phenylpyrazole of formula IV:

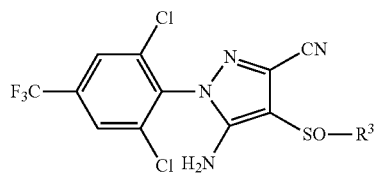

wherein R³ is —CF₃ (fipronil) or —C₂H₅ (ethiprole);
and extenders and/or surface active agents,
wherein the animal pest is from the order of Coleoptera, Lepidoptera, or Homoptera.

28. The method according to claim 27 wherein the plant part is a seed.

29. The method according to claim 27 wherein the composition consists essentially of Isotianil and the at least one active substance and extenders and/or surface active agents.

30. The method according to claim 27 wherein there is one said active substance.

31. The method according to claim 29 wherein the composition consists of Isotianil, one said active substance and extenders/and or surface active agents.

32. The method according to claim 27, wherein the animal pest is *Myzus persicae*.

33. The method according to claim 27, wherein the animal pest is *Phaedon cochleariae*.

34. The method according to claim 27, wherein the animal pest is *Plutella xylostella*.

35. The method according to claim 27, wherein the animal pest is *Spodoptera frugiperda*.

36. The method according to claim 30, wherein the animal pest is *Myzus persicae* and the one active substance is a neonicotinyl.

37. The method according to claim 30, wherein the animal pest is *Phaedon cochleariae* and the one active substance is a neonicotinyl.

38. The method according to claim 30, wherein the animal pest is *Plutella xylostella* and the one active substance is a neonicotinyl.

39. The method according to claim 30, wherein the animal pest is *Spodoptera frugiperda* and the one active substance is a neonicotinyl or a phenylpyrazole.

* * * * *